United States Patent
Kastner et al.

(10) Patent No.: US 7,034,158 B2
(45) Date of Patent: *Apr. 25, 2006

(54) METHOD OF PRODUCING BIPERIDEN I

(75) Inventors: Gerhard Kastner, Ludwigshafen (DE); Klaus Scheib, Dannstadt-Schauernheim (DE)

(73) Assignee: Abbott GmbH & Co. KG, Wiesbaden (DE)

( * ) Notice: Subject to any disclaimer, the term of this patent is extended or adjusted under 35 U.S.C. 154(b) by 12 days.

This patent is subject to a terminal disclaimer.

(21) Appl. No.: 10/477,767

(22) PCT Filed: May 17, 2002

(86) PCT No.: PCT/EP02/05498

§ 371 (c)(1),
(2), (4) Date: Apr. 8, 2004

(87) PCT Pub. No.: WO02/094801

PCT Pub. Date: Nov. 28, 2002

(65) Prior Publication Data

US 2005/0176963 A1    Aug. 11, 2005

(30) Foreign Application Priority Data

May 18, 2001    (DE) .................. 101 24 452

(51) Int. Cl.
*C07D 211/04*    (2006.01)
(52) U.S. Cl. .................................... 546/205
(58) Field of Classification Search ............... 546/205
See application file for complete search history.

(56) References Cited

U.S. PATENT DOCUMENTS

| 2,789,110 A | 4/1957 | Klavehn |
| 6,835,839 B1 * | 12/2004 | Klein et al. .................. 546/205 |

FOREIGN PATENT DOCUMENTS

| DE | 1 0 05 067 | 3/1957 |
| JP | 11189729 A | 7/1999 |
| WO | WO 02/094800 | 5/2002 |

OTHER PUBLICATIONS

Ronald Breslow and Uday Maitra, On the Origin of Product Selectivity in Aqueous Dies-Alder Reactions, Tetrahedron Letters. vol. 25. No. 12, pp 1239-1240, 1984, Great Britain.
Ullmans Enzykopadie der technischen Chemie, 4$^{th}$ Edition, vol. 21, Verlag Chemie, 1982, p. 627.
J. G. Dinwiddie and S. P. McManus (J. Org. Chem., 1965, 30, 766).

* cited by examiner

*Primary Examiner*—Rita Desai
(74) *Attorney, Agent, or Firm*—Wood, Phillips, Katz, Clark & Mortimer

(57) ABSTRACT

The invention relates to a method for producing biperiden which is characterized in that an exo/endo mixture of 1-(bicyclo[2.2.1]hept-5-en-2-yl)-3-piperidino-1-propanone is reacted with an isomer ratio of the exo form to the endo form of at least 2.5:1 with diphenyl magnesium, an isomer mixture containing biperiden is obtained therefrom and biperiden is produced therefrom.

16 Claims, No Drawings

US 7,034,158 B2

METHOD OF PRODUCING BIPERIDEN I

CROSS-REFERENCE TO RELATED APPLICATION

This application is a Section 371 National Stage Application of Application No. PCT/EP02/05498 filed on May 17, 2002.

The present invention relates to a method for producing biperiden.

Biperiden is a well-known central anticholinergic agent and is employed for the treatment of Parkinson's disease (Ullmanns Enzyklopädie der technischen Chemie, 4th edition, volume 21, Verlag Chemie, 1982, p. 627). It comprises a racemate of 1-(bicyclo[2.2.1]hept-5-en-2-yl(exo,R))-1-phenyl-3-piperidino-propanol(1,S) and 1-(bicyclo[2.2.1]hept-5-en-2-yl(exo,S))-1-phenyl-3-piperidinopropanol(1,R) (Ia) and represents one of four possible pairs of enantiomers (Ia–d) of the amino alcohol 1-(bicyclo[2.2.1]hept-5-en-2-yl)-1-phenyl-3-piperidino-1-propanol (I).

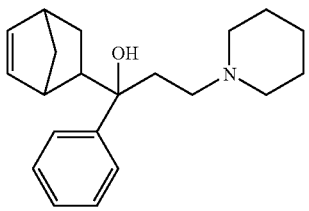

(I)

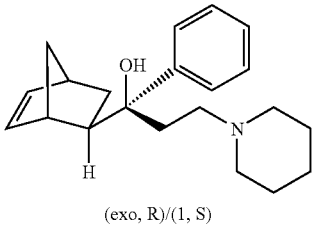

(exo, R)/(1, S)

(Ia)

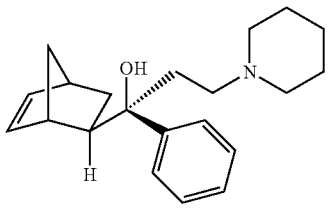

(exo, S)/(1, R)

(Ib)

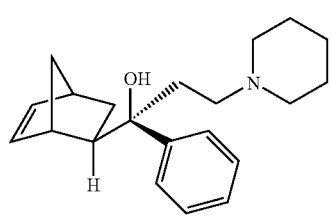

(exo, R)/(1, R)

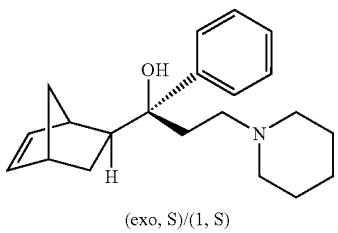

(exo, S)/(1, S)

(Ic)

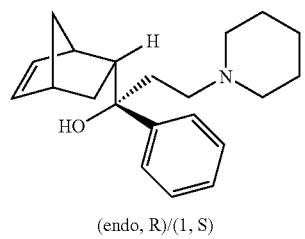

(endo, R)/(1, S)

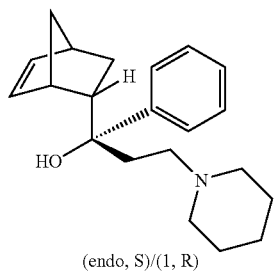

(endo, S)/(1, R)

(Id)

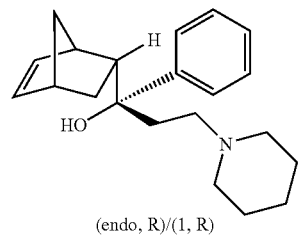

(endo, R)/(1, R)

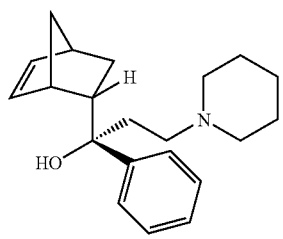

(endo, S)/(1, S)

DE 1 005 067 and U.S. Pat. No. 2,789,110 describe the preparation of the amino alcohol I by reacting 1-(bicyclo[2.2.1]hept-5-en-2-yl)-3-piperidino-1-propanone (II) with a phenylmagnesium halide. U.S. Pat. No. 2,789,110 additionally describes the preparation of the propanone II starting from 1-(bicyclo[2.2.1]hept-5-en-2-yl)-ethanone (III), paraformaldehyde and piperidine hydrochloride in a Mannich reaction, and the preparation of the ethanone III from cyclopentadiene and methyl vinyl ketone in a Diels-Alder cycloaddition.

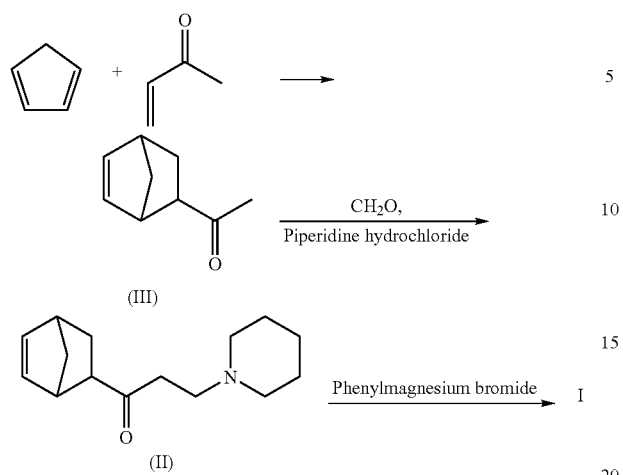

(III)

(II)

Neither DE 1 005 067 nor U.S. Pat. No. 2,789,110 disclose whether the amino alcohol I obtained in this way is a mixture of isomers or a pure isomer.

The precursor for preparing the propanol, 1-(bicyclo[2.2.1]hept-5-en-2-yl)-3-piperidino-1-propanone (II), can exist in two isomeric forms, as exo or as endo isomer (II-exo, II-endo), and only the exo form is able to afford biperiden in the abovementioned reaction with a phenylmagnesium halide.

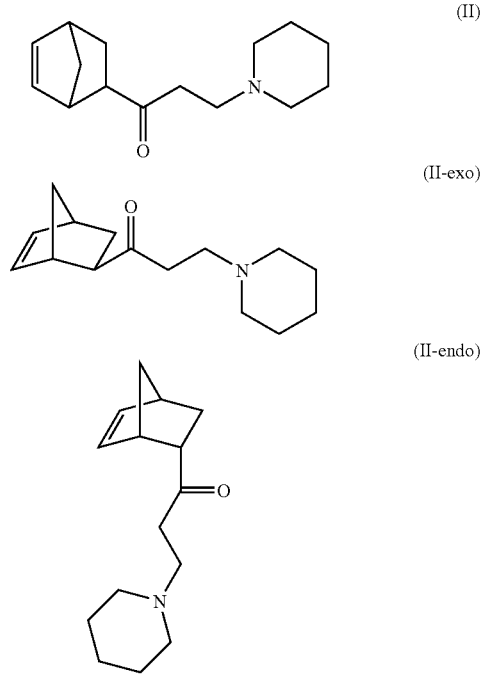

The structural formulae of II-exo and of II-endo show for the sake of simplicity in each case only one of two possible enantiomers of the exo isomer and endo isomer, respectively. However, the designation II-exo or II-endo relates hereinafter to the pair of enantiomers of the exo or endo form.

1-(Bicyclo[2.2.1]hept-5-en-2-yl)ethanone (III), the starting substance for synthesizing the propanone II, may also exist both as exo and as endo isomer (III-exo, III-endo) and, correspondingly, only reaction of the exo isomer leads in the subsequent steps to biperiden.

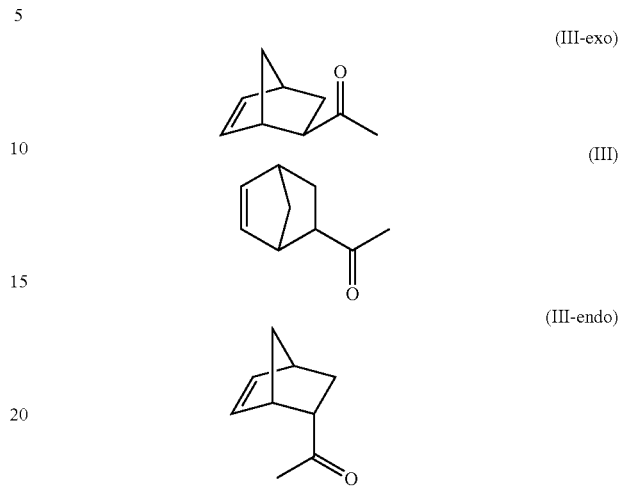

The structural formulae of III-exo and of III-endo show for the sake of simplicity in each case only one of two possible enantiomers of the exo isomer and endo isomer, respectively. However, the designation III-exo or III-endo relates hereinafter to the pair of enantiomers of the exo or endo form.

It is not possible to infer any information about the configuration of the precursors III and intermediates II employed in any of the abovementioned publications.

It is known that 1-(bicyclo[2.2.1]hept-5-en-2-yl)ethanone (III) is obtained from the cycloaddition in an exo/endo ratio of 1:4 (e.g. R. Breslow, U. Maitra, Tetrahedron Letters, 1984, 25, 1239). Since the prior art mentioned at the outset makes no statements at all about the stereochemistry of the ethanone III, it must be assumed that the ethanone III was employed in this ratio of isomers to prepare the amino alcohol I.

The preparation of exo-1-(bicyclo[2.2.1]hept-5-en-2-yl) ethanone (III-exo) was described in 1965 by J. G. Dinwiddie and S. P. McManus (J. Org. Chem., 1965, 30, 766). This entails exo/endo mixtures of 1-(bicyclo[2.2.1]hept-5-en-2-yl)ethanone (III) in which the endo content predominates being heated in methanol in the presence of sodium methanolate and isomerizing to mixtures with an exo content of about 70%. It is possible to obtain from this by fractional distillation and, where appropriate, redistillation of the distillate exo-1-(bicyclo[2.2.1]hept-5-en-2-yl)ethanone (III-exo) with a purity of up to 95%.

Experiments by the applicant have shown that even on use of virtually pure exo-1-(bicyclo[2.2.1]hept-5-en-2-yl)ethanone (III-exo), i.e. of an ethanone III with an exo content of at least 95%, as starting material it is possible to obtain pure biperiden (Ia) in only low yields, with in particular the reaction of 1-(bicyclo[2.2.1]hept-5-en-2-yl)-3-piperidino-1-propanone (II) with a phenylmagnesium halide proceeding with a poor yield of biperiden (Ia). Pure biperiden means a biperiden (Ia) with a purity of at least 99.0%, as is generally necessary for pharmaceutical applications.

It is an object of the present invention to provide a method for producing biperiden which affords the latter in a higher yield. Biperiden is intended to mean a substance of the structural formula Ia.

It has been possible to achieve the object by a method for producing biperiden (Ia) in which an exo/endo mixture of 1-bicyclo[2.2.1]hept-5-en-2-yl)-3-piperidino-1-propanone (II) with a ratio of the exo-form to the endo-form isomers of at least 2.5:1, preferably of at least 3.0:1 and in particular of about 3.5–4.0:1, is reacted with diphenylmagnesium, resulting in a biperiden-containing mixture of isomers, and isolating biperiden (Ia) therefrom.

The exo and endo isomers employed in the method of the invention comprise, as already described for the exo and endo ethanone III-exo and III-endo and for the exo and endo propanone II-exo and II-endo, pairs of enantiomers. In order to obtain biperiden (Ia), which is itself a racemate, racemic mixtures of enantiomers of the starting materials and of the intermediates are employed. However, the method of the invention can also be applied to pure enantiomers and to non-racemic mixtures of enantiomers.

The reaction of diphenylmagnesium with the exo/endo mixture of the propanone II suitably takes place in a solvent customary for Grignard reactions. These include benzene, toluene, xylenes, acyclic or cyclic ethers having 4- to 6 C atoms, mixtures thereof or mixtures of them with aliphatic or alicyclic hydrocarbons such as n-hexane or cyclohexane. Examples of suitable acyclic ethers are diethyl ether and tert-butyl methyl ether, and examples of suitable cyclic ethers are tetrahydrofuran and dioxane. Diethyl ether, tetrahydrofuran or dioxane or mixtures thereof are preferably used. The solvents are usually employed anhydrous, as normal for Grignard reactions.

Diphenylmagnesium and 1-(bicyclo[2.2.1]hept-5-en-2-yl)-3-piperidino-1-propanone (II) are ordinarily employed in a molar ratio in the range from 0.8:1 to 3:1, preferably in the range from 0.8:1 to 2:1, in particular in the range from 0.8:1 to 1.5:1. It is particularly preferable for II to be reacted with diphenylmagnesium in virtually equimolar amounts.

Ordinarily, the propanone II is added to diphenylmagnesium in the form of a solution in one of the abovementioned organic solvents at a temperature in the range from −20° C. to the boiling point, in particular in the range from −10° C. to 90° C. and particularly preferably in the range from 0° C. to 70° C. Diphenylmagnesium is moreover ordinarily employed in a concentration in the range from 0.1 to 10 mol/l, preferably in the range from 0.1 to 3 mol/l and particularly preferably in the range from 0.2 to 2 mol/l.

The propanone II can be added in one portion or, preferably, over a period of from a few minutes up to several hours, e.g. 5 minutes to 5 hours. The propanone II is added either in the form of a solution in one of the abovementioned inert solvents suitable for Grignard reactions or, preferably, in pure form. When added as solution, the concentration of the propanone II is ordinarily from 0.1 to 20 mol/l, preferably 1 to 15 mol/l. To complete the reaction, the reaction mixture is normally left at a temperature in the range from −20° C. to the boiling point of the reaction mixture, preferably in the range from −10° C. to 90° C. and particularly preferably in the range from 10° C. to 80° C. for from 15 minutes to 5 hours, specifically 30 minutes to 2 hours, during which it is preferably stirred to improve mixing. Workup is, as usual for Grignard reactions, by aqueous extraction, e.g. by quenching the reaction mixture with water, an aqueous ammonium chloride solution or an acidic aqueous solution, with the pH of the resulting mixture in the latter case subsequently being made alkaline, extracting the quenched mixture, where appropriate after removal of an organic phase, with a water-immiscible solvent suitable for dissolving the product, and removing the solvent from the extract or from the extract combined with the organic phase.

Examples of suitable solvents are aromatic compounds such as benzene or toluene, the abovementioned acyclic ethers, esters such as ethyl acetate or chlorine-containing aliphatic compounds such as dichloromethane or trichloromethane.

The diphenylmagnesium employed in the method of the invention is produced in a manner known per se. For example, dioxane can be added to a phenylmagnesium halide, e.g. phenylmagnesium chloride, in a suitable solvent, thus shifting the Schlenk equilibrium to result in diphenylmagnesium and the corresponding magnesium halide-dioxane complex. The latter usually precipitates, but is preferably not removed from the solution. Suitable solvents are generally acyclic and cyclic ethers preferably having 4 to 6 C atoms or mixtures thereof with aliphatic, alicyclic or aromatic hydrocarbons. Examples of suitable acyclic ethers are diethyl ether and tert-butyl methyl ether, and a suitable cyclic ether is tetrahydrofuran. The suitable aliphatic and alicyclic hydrocarbons include in particular n-hexane and cyclohexane, and examples of suitable aromatic hydrocarbons are benzene, toluene and xylenes.

Dioxane is ordinarily employed at least equimolar in relation to the phenylmagnesium halide; dioxane is preferably employed in excess, for example in an excess of from 50 to 500 mol %, in particular from 100 to 300 mol % and specifically of from 100 to 200 mol %.

The dioxane is added to the solution of the phenylmagnesium halide usually at a temperature in the range from −20 to 60° C., preferably in the range from −10 to 40° C.

The mixture obtained after addition of the dioxane is normally left for from 15 minutes to 2 hours, preferably 20 minutes to one hour, in the temperature range mentioned for the addition of the dioxane, before it is employed in the method of the invention.

Both the preparation of diphenylmagnesium and the Grignard reaction with the propanone II are suitably carried out under an inert gas atmosphere. Examples of suitable inert gases are nitrogen and the noble gases such as argon, and mixtures thereof.

The crude product obtained from the reaction according to the invention of the propanone II with diphenylmagnesium consists essentially of the four diastereomeric pairs of enantiomers Ia to Id of the 1-(bicyclo[2.2.1]hept-5-en-2-yl)-1-phenyl-3-piperidino-1-propanol (I), with the pair of isomers Ia comprising at least 50% of the mixture of isomers. When the propanone II with an exo/endo ratio of about 3.5:1 is employed, the crude product contains the pairs of enantiomers in a ratio, determined by gas chromatography, of biperiden (Ia) to form Ib to form Ic to form Id of about 10.4:3.4:3.0:1. The proportion of biperiden (Ia) in the mixture of isomers is in this case 58%.

The biperiden (Ia) is isolated from the mixture of diastereomers by dissolving the latter with heating, preferably at a temperature of from 40 to 80° C., in particular from 50 to 70° C., in aqueous isopropanol, preferably in 70 to 95% isopropanol, particularly preferably in 90% isopropanol, and precipitating the hydrochloride by addition of HCl in the temperature range mentioned, for example in the form of the solution of hydrogen chloride in isopropanol or as hydrochloric acid, and removing the hydrochloride from the solution. To complete the salt formation after the addition of HCl is complete, the mixture is preferably stirred at a temperature from 50° C. to the boiling point of the reaction mixture for about 0.5 to 3 hours. The mixture is then cooled to a temperature in the range from 0 to 30° C., where appropriate stirred in this temperature range for up to several hours, and then the hydrochloride which has formed is isolated from the solution. The percentage data given here and hereinafter concerning the isopropanol content relate to the volume of the isopropanol based on the total volume of the water-containing solvent. HCl is employed at least equimolar in relation to the amino alcohol I, preferably in an excess of from 5 to 50 mol % and particularly preferably from 5 to 20 mol %. For further purification, the precipitate is stirred with aqueous isopropanol, preferably with 70 to 95% isopropanol, particularly preferably with 90% isopropanol, at elevated temperature, preferably at 40 to 80° C., in particular at the boiling point of the mixture, for about 0.5 to 3 hours and then cooled to a temperature in the range from 0 to 30° C., where appropriate stirred in this temperature range for up to several hours, and then the purified hydrochloride is filtered off. For further purification, the hydrochloride purified in this way is converted into the corresponding free base at elevated temperature, preferably at 40 to 60° C., e.g. at 50° C., in a $C_1$–$C_2$-alcohol or a mixture thereof, preferably in methanol, with an at least equimolar amount of a suitable base. Suitable bases are alkali metal or alkaline earth metal hydroxides and alkali metal carbonates; sodium or potassium hydroxide or their aqueous solutions are preferably used, and sodium hydroxide or sodium hydroxide solution is particularly preferably used. However, it is also possible to use water-soluble organic bases, for example amines having aliphatic substituents with 2 to 8 C atoms. To complete the reaction, completion of the addition of the base is preferably followed by stirring in the temperature range for the addition of the base for about 0.5 to 3 hours. The reaction mixture is then cooled to a temperature in the range from 0 to 30° C. and, where appropriate, stirred in this temperature range for up to several hours. The solid substance is then filtered off, washed with water and subsequently stirred at elevated temperature, preferably at 40 to 80° C., in particular at the boiling point of the mixture, in a $C_1$–$C_2$-alcohol or a mixture thereof, preferably in methanol, for about 0.5 to 3 hours, the mixture is then cooled to a temperature in the range from 0 to 30° C., where appropriate stirred in this temperature range for up to several hours, and then the solid is removed in a suitable way, for example by filtration. Biperiden (Ia) with a purity of at least 99.0% is obtained in this way.

It is possible by the use according to the invention of diphenylmagnesium in place of the phenylmagnesium halide employed in the prior art to increase the yield of biperiden (Ia) considerably.

Biperiden (Ia) can then be converted with a pharmacologically acceptable acid in a conventional manner into its acid addition salt. Examples of suitable acids are hydrohalic acids, in particular hydrogen chloride or hydrochloric acid, and organic mono- or dicarboxylic acids such as acetic acid, oxalic acid, maleic acid, fumaric acid, lactic acid, tartaric acid, adipic acid or benzoic acid, also phosphoric acid and sulfuric acid, and the acids mentioned in "Fortschritte der Arzneimittelforschung, volume 10, pages 224 et seq., Birkhäuser Verlag, Basle, Stuttgart, 1966". Biperiden (Ia) is normally marketed as hydrochloride.

The 1-(bicyclo[2.2.1]hept-5-en-2-yl)-3-piperidino-1-propanone (II) employed in the Grignard reaction is obtained by reacting exo-1-(bicyclo[2.2.1]hept-5-en-2-yl)ethanone (III-exo) in a Mannich reaction in the presence of an acid with piperidine and a formaldehyde source or with the adduct of piperidine and formaldehyde, preferably in a suitable solvent.

Hereinafter, exo-1-(bicyclo[2.2.1]hept-5-en-2-yl)ethanone (III-exo) is intended to mean an ethanone III in which the proportion of exo is at least 96%.

Suitable solvents are, in particular, $C_1$–$C_4$-alkanols, e.g. methanol, ethanol, n-propanol, isopropanol, sec-butanol and isobutanol. Isopropanol is preferably used. The exo ethanone (III-exo) and piperidine are usually employed in a molar ratio in the range from 0.5:1 to 1.5:1, preferably 1:1. Formaldehyde is normally present in excess, it being possible for the excess to be up to 100 mol % based on piperidine, in particular up to 50 mol %. Formaldehyde can in this connection be employed either gaseous, as formalin, as trioxane or as paraformaldehyde. It is preferred to use paraformaldehyde, in particular in combination with piperidinium chloride. In a preferred procedure, the exo ethanone (III-exo), piperidine hydrochloride and paraformaldehyde are reacted together in molar ratios of 1:0.9-1.2:1-1.4. The solvent preferably used in this case is a $C_1$–$C_4$-alkanol, especially isopropanol. The reaction temperature is ordinarily in the range from 10° C. to the boiling point of the mixture. Heating to reflux is preferred.

The workup takes place in a manner known per se. For this purpose, usually first the solvent is removed under reduced pressure, and the residue is taken up in water. The aqueous solution obtained in this way is extracted with a suitable organic solvent, i.e. with a water-immiscible, moderately polar solvent, for example an aliphatic ether having 4 to 6 C atoms, such as diethyl ether, tert-butyl methyl ether or preferably diisopropyl ether. This extraction normally takes place at pH $\leq 7$ and serves to remove byproducts. In particular, extraction of the acidic aqueous mixture obtained after removal of the solvent and dilution with water is first carried out, then the pH of the aqueous phase is raised by adding small amounts of base, and extraction is repeated, with a pH of $\leq 7$ being maintained.

The aqueous phase is then preferably made alkaline by adding base in one or more stages, preferably to pH $\geq 7.5$, in particular pH 7.5 to 9 and specifically pH 8.0 to 8.5, in order to convert the 1-(bicyclo-[2.2.1]-hept-5-en-2-yl)-3-piperidino-1-propanone (II), which is still in the form of the acid addition salt, into the free amine. Bases suitable for this purpose are the usual inorganic bases such as KOH, NaOH, $Na_2CO_3$, $K_2CO_3$ and the like. The aqueous phase is then extracted one or more times with one of the abovementioned water-immiscible moderately polar solvents, preferably diisopropyl ether. To isolate the propanone II from the extract, the solvent is removed, where appropriate under reduced pressure. For further purification, the residue can be purified by a vacuum distillation under a pressure of preferably less than 10 mbar, particularly preferably less than 5 mbar and in particular less than 1 mbar. The resulting mixture consists of exo- and endo-1-(bicyclo-[2.2.1]hept-5-en-2-yl)-3-piperidino-1-propanone (II) in a ratio of at least 2.5:1, preferably of at least 3.0:1 and in particular of 3.5-4.0:1.

The exo-1-(bicyclo[2.2.1]hept-5-en-2-yl)ethanone (III-exo) used to prepare the 1-(bicyclo[2.2.1]hept-5-en-2-yl)-3-piperidino-1-propanone (II) is obtained by a Diels-Alder cycloaddition reaction of cyclopentadiene and methyl vinyl ketone. Cyclopentadiene and methyl vinyl ketone are normally employed in a molar ratio in the range from 3.0:1 to 0.5:1. They are preferably reacted equimolar or with cyclopentadiene in excess, with the excess preferably being 50 to 150 mol %.

The reaction is usually carried out at a temperature in the range from 0 to 60° C., preferably in the range from 20 to 40° C.

The cycloaddition can be carried out in a solvent conventional for such reactions, such as diethyl ether, benzene, toluene or xylene or else without solvent. It is preferred to use no solvent.

Low-boiling constituents, usually unreacted precursors and, when employed, solvent, are usually removed following the cycloaddition by distillation under reduced pressure, preferably under 1 to 150 mbar. The remaining mixture, which consists of about 20% exo- and about 80% endo-1-(bicyclo[2.2.1]hept-5-en-2-yl)ethanone, is reacted with an alkali metal $C_1$–$C_4$-alcoholate. The amount of alkali metal alcoholate is usually from 0.1 to 5% by weight, preferably from 0.2 to 2% by weight, based on the total weight of the mixture. Sodium methanolate is preferably used. The temperature necessary for isomerization of the ethanone III is usually in the range from 50 to 110° C., preferably in the range from 60 to 100° C. For this purpose, the mixture is often heated under reduced pressure to reflux, preferably under a pressure of from 1 to 100 mbar and in particular under a pressure of from 5 to 50 mbar.

These conditions are usually applied for from 10 minutes to 5 hours, in particular 20 minutes to 3 hours and specifically 0.5 hours to 2 hours, and then fractional distillation of the resulting mixture is started, preferably distilling out the exo isomer of III. It is assumed that removal of the exo isomer from the equilibrium promotes isomerization of the endo ethanone to the exo form. The fractional distillation normally takes place through a column under reduced pressure, preferably in the range from 1 to 100 mbar, in particular from 1 to 50 and specifically from 1 to 20 mbar. The distillation temperature (distillate temperature) is preferably adjusted to from 50 to 100° C. and specifically to 50 to 80° C. In this way, exo-1-(bicyclo[2.2.1]-hept-5-en-2-yl)ethanone (III-exo) is obtained in a purity which is at least 96%. Redistillation of the distillate results in the exo ethanone III-exo with a purity of up to 100%.

The following examples serve to illustrate the invention but are not to be understood as restrictive.

EXAMPLES

1. Preparation of the Starting Material 1.1 exo-1-(Bicyclo[2.2.1]hept-5-en-2-yl)ethanone (III-exo)

198.3 g of cyclopentadiene were rapidly added to 210.3 g of methyl vinyl ketone. After the addition was complete, the solution was stirred at room temperature for one hour and then unreacted precursor was removed by distillation at a temperature of 58° C. and a pressure of 20 mbar. The residue from evaporation, mainly consisting of a mixture of the exo and the endo form of 1-(bicyclo[2.2.1]hept-5-en-2-yl)ethanone (III) in the ratio of 1:4, was heated to reflux with 5 g of sodium methanolate under a pressure of from 10 to 20 mbar for one hour. The reaction mixture was then distilled through a column at a temperature of 75° C. and a pressure of 20 mbar. This resulted in 298.3 g (73% of theory) of exo-1-(bicyclo[2.2.1]hept-5-en-2-yl)ethanone (III-exo) in the form of a pale yellowish oil.

1.2 1-(Bicyclo[2.2.1]hept-5-en-2-yl)-3-piperidino-1-propanone (II)

68.1 g of exo-1-(bicyclo[2.2.1]hept-5-en-2-yl)ethanone (III-exo), 60.8 g of piperidine hydrochloride and 18 g of paraformaldehyde were heated to reflux in 140 ml of isopropanol for five hours. The solvent was removed in vacuo, and the residue was taken up in 100 ml of water. The solution was washed three times with 50 ml of diisopropyl ether each time and then adjusted to pH 10 with 50% strength sodium hydroxide solution. Three extractions each with 50 ml of diisopropyl ether were carried out, the three extracts were combined and the solvent was removed in a rotary evaporator. The residue from evaporation was distilled in a Kugelrohr at 75° C. under high vacuum at 0.001 mbar. The distillate obtained consisted of 50.2 g (43% of theory) of a mixture of exo- and endo-1-(bicyclo[2.2.1]hept-5-en-2-yl)-3-piperidino-1-propanone (II) in the ratio 3.5:1 in the form of a colorless oil.

2. Preparation of Biperiden (Ia)

603.6 g (6.85 mol) of dioxane were added to 1 500 g of a 25% strength solution of phenylmagnesium chloride (375 g, 2.74 mol) in tetrahydrofuran while cooling to 0° C. in an ice bath, during which a white precipitate formed. After stirring while cooling in the ice bath for 30 min, 320 g (1.37 mol) of the 3.5:1 mixture obtained as in 1.2 of the exo and endo forms of 1-(bicyclo[2.2.1]hept-5-en-2-yl)-3-piperidino-1-propanone (II) were added while cooling in the ice bath. After the addition was complete, the ice bath was removed and the mixture was stirred at room temperature for one hour. The solution was subsequently added slowly to 1 500 ml of ice-cold water and then extracted three times with 500 ml of toluene each time. The organic phases were combined, dried over sodium sulfate and evaporated on a rotary evaporator. The residue from evaporation, 433.8 g of a mixture which consisted essentially of forms Ia to Id of 1-(bicyclo[2.2.1]hept-5-en-2-yl)-1-phenyl-3-piperidino-1-propanol (I) in the ratio (GC) 10.4:3.4:3.0:1, was dissolved in 3 500 ml of hot 90% isopropanol, and 228 ml of a 6-molar solution of hydrogen chloride in isopropanol were added to the solution at 60° C. After the addition of acid, the mixture was stirred at 60° C. for one hour and then at the reflux temperature for 0.5 hours. After cooling to room temperature, the crystals which had separated out were removed, washed with 700 ml 90% isopropanol and dried in vacuo at 70° C. The hydrochloride obtained in this way was kept at the reflux temperature in 1000 ml of 90% isopropanol for 0.5 hours. After cooling to room temperature, the solid was removed, washed with 700 ml of 90% isopropanol and dried in vacuo at 70° C. The hydrochloride purified in this way was introduced into 600 ml of methanol and, at 50° C., 60 ml of 30% strength sodium hydroxide solution were added. The mixture was stirred at 50° C. for an hour, and the solid was then removed after cooling to room temperature, washed with 200 ml of water and dried in vacuo at 40° C. The base obtained in this way was kept at the reflux temperature in 250 ml of methanol for an hour. After cooling to room temperature, the solid product was removed, washed with 75 ml of methanol and dried in vacuo at 40° C. 85.3 g of biperiden (Ia) were obtained as colorless crystals of melting point 112 to 114° C. (Ullmanns Enzyklopädie der techn. Chemie, 4th Edition, Volume 21, Verlag Chemie, 1982, page 627: 112–114° C.); which is 20% of theory.

3. Comparative Example B

Preparation of Biperiden (Ia)

320 g (1.37 mol) of the 3.5:1 mixture obtained as in 1.2 of the exo and endo forms of 1-(bicyclo[2.2.1]hept-5-en-2-yl)-3-piperidino-1-propanone (II) were added to 2740 ml of a 1.0 molar solution of phenylmagnesium bromide in diethyl ether (2.74 mol of phenylmagnesium bromide) while cooling to 0° C. in an ice bath.

After the addition was complete, the ice bath was removed and the mixture was stirred at room temperature for one hour. The solution was subsequently added slowly to 1 500 ml of ice-cold water and then extracted three times with 500 ml of toluene each time. The organic phases were combined and dried over sodium sulfate, and the solvent was removed in a rotary evaporator. The residue from evaporation, 314.3 g (74% of theory) of a mixture which consisted essentially of forms Ia to Id of 1-(bicyclo[2.2.1]hept-5-en-2-yl)-1-phenyl-3-piperidino-1-propanol (I) in the ratio (GC) 6.1:3.4:1.7:1, was dissolved in 3 500 ml of hot 90% isopropanol and, at 60° C., 228 ml of a 6-molar solution of hydrogen chloride in isopropanol were added to the solution.

After the addition of acid, the mixture was stirred at 60° C. for one hour and at the reflux temperature for 0.5 hours. After cooling to room temperature, the crystals which had separated out were removed, washed with 700 ml of 90% isopropanol and dried in vacuo at 70° C. The hydrochloride obtained in this way was kept at the reflux temperature in 1 000 ml 90% isopropanol for 0.5 hours. After cooling to room temperature, the solid was removed, washed with 700 ml of 90% isopropanol and dried in vacuo at 70° C. The hydrochloride purified in this way was introduced into 600 ml of methanol and, at 50° C., 60 ml of 30% strength sodium hydroxide solution were added. The mixture was stirred at 50° C. for one hour, and the solid was removed after cooling to room temperature, washed with 200 ml of water and dried in vacuo at 40° C. The base obtained in this way was heated to reflux in 250 ml of methanol for one hour. After cooling to room temperature, the solid product was removed, washed with 75 ml of methanol and dried in vacuo at 40° C. 42.7 g of biperiden (Ia) were obtained as colorless crystals of melting point 112 to 114° C. (Ullmanns Enzyklopädie der techn. Chemie, 4th Edition, Volume 21, Verlag Chemie, 1982, page 627: 112–114° C.), which is 10% of theory.

4. Preparation of Biperiden Hydrochloride 6.7 g of biperiden (Ia) were dissolved in 75 ml of isopropanol by heating to the reflux temperature. The solution was filtered hot, and the filter was washed with 7 ml of isopropanol. 4.7 ml of 5-molar hydrochloric acid were added to the combined filtrates at 75° C. The mixture was then heated to reflux for 15 minutes. After cooling to room temperature, the precipitated solid was filtered off with suction, washed with 7 ml of isopropanol and dried in vacuo at 70° C. 7.3 g of biperiden hydrochloride were obtained in the form of colorless crystals of melting point 278 to 280° C. (Ullmanns Enzyklopädie der techn. Chemie, 4th edition, volume 21, Verlag Chemie, 1982, page 627: 278–280° C.); which is 98% of theory.

We claim:

1. A method for producing biperiden, characterized in that an exo/endo mixture of 1-(bicyclo[2.2.1]hept-5-en-2-yl)-3-piperidino-1-propanone with a ratio of the exo-form to the endo-form isomers of at least 2.5:1 is reacted with diphenylmagnesium, resulting in a biperiden-containing mixture of isomers from which biperiden is isolated.

2. The method as claimed in claim 1, characterized in that diphenylmagnesium and 1-(bicyclo[2.2.1]hept-5-en-2-yl)-3-piperidino-I-propanone are employed in a molar ratio of from 0.8:1 to 3:1.

3. The method of claim 1, characterized in that the reaction of diphenylmagnesium with 1-(bycyclo[2.2.1]-hept-5-en-2-yl)-3-piperidino-1-propanone is carried out at a temperature of from −20° C. to the boiling point of the reaction mixture.

4. The method of claim 3, characterized in that the reaction of diphenylmagnesium with 1-(bicyclo[2.2.1]-hept-5-en-2-yl)-3-piperidino-1-propanone is carried out at a temperature of from −10° C. to 90° C.

5. The method of claim 1, characterized in that the reaction of diphenylmagnesium with 1-(bicyclo[2.2.1]hept-5-en-2-yl)-3-piperidino-1-propanone is carried out in the presence of a cyclic ether.

6. The method of claim 1, characterized in that 1-(bicyclo[2.2.1]hept-5-en-2-yl)-3-piperidino-1-propanone is added to a solution of diphenylmagnesium.

7. The method of claim 1, characterized in that to isolate biperiden (Ia) the mixture of isomers of 1-(bicyclo[2.2.1]hept-5-en-2-yl)-1-phenyl-40 3-piperidino-1-propanol obtained in the reaction of the exo/endo mixture of 1-(bicyclo[2.2.1]hept-5-en-2-yl)-3-piperidino-1-propanone with diphenylmagnesium is converted into the hydrochloride at elevated temperature in aqueous isopropanol, the precipitated hydrochloride is isolated, suspended in aqueous isopropanol at elevated temperature and again isolated after cooling, the hydrochloride obtained in this way is converted into the corresponding free base at elevated temperature in a $C_1$–$C_2$-alkanol or in a mixture thereof with a base after cooling, the base which has formed is isolated and washed with water, and the base obtained in this way is suspended at elevated 20 temperature in a $C_1$–$C_2$-alkanol or in a mixture thereof and, after cooling, biperiden is isolated by removing the solid from the mother liquor.

8. The method of claim 1, characterized in that 1-(bicyclo[2.2.1]hept-5-en-2-yl)-3-piperidino-1-propanone is prepared by a) reacting cyclopentadiene and methyl vinyl ketone together and obtaining an exo/endo mixture of 1-(bicyclo[2.2.1]hept-5-en-2-yl)ethanone, b) heating this mixture of isomers with an alkali metal $C_1$–$C_4$-alcoholate, and obtaining exo-1-(bicyclo[2.2.1]hept-5-en-2-yl)ethanone by fractional distillation, c) reacting this exo-1-(bicyclo[2.2.1]hept-5-en 2-yl)ethanone in the presence of an acid with piperidine and of a formaldehyde source, and obtaining an exo/endo mixture of 1-(bicyclo[2.2.1]hept-5-en-2-yl)-3-piperidino-1-propanone.

9. The method of claim 8, characterized in that from 0.1 to 5% by weight of alkali metal alcoholate, based on the total weight of the mixture, is employed in step b).

10. The method of claim 8, characterized in that in step b) there is heating to reflux under a pressure of from 1 to 100 mbar for from 10 minutes to 5 hours.

11. The method of claim 8, characterized in that exo-1-(bicyclo[2.2.1]hept-5-en-2-yl)ethanone is obtained in step b) by distillation through a column under a pressure of from 1 to 100 mbar and at a temperature of from 30 to 110° C.

12. The method of claim 8, characterized in that sodium methanolate is used in step b).

13. The method of claim 8, characterized in that paraformaldehyde is used as formaldehyde source in step c).

14. The method of claim 13, characterized in that piperidine hydrochloride is used in step c).

15. The method of claim 8, characterized in that formaldehyde is employed in excess in step c).

16. 1-(Bicyclo[2.2.1]hept-5-en-2-yl)-3-piperidino-1-propanone with an exo/endo ratio of from 2.5:1 to 4.0:1.

* * * * *

UNITED STATES PATENT AND TRADEMARK OFFICE
CERTIFICATE OF CORRECTION

| | | |
|---|---|---|
| PATENT NO. | : 7,034,158 B2 | Page 1 of 1 |
| APPLICATION NO. | : 10/477767 | |
| DATED | : April 25, 2006 | |
| INVENTOR(S) | : Gerhard Kastner et al. | |

It is certified that error appears in the above-identified patent and that said Letters Patent is hereby corrected as shown below:

Foreign Application Priority Data designation (30) shown as:

DE 101 24 452 filed May 18, 2001 should be corrected to show priority as:

DE 101 24 452.5 filed May 18, 2001 and
    DE 101 24 450.9 filed May 18, 2001

Claim 3, column 11, line 60 reads as:

reaction of diphenylmagnesium with 1-(bycyclo[2.2.1]- should be correct to read as:

reaction of diphenylmagnesium with 1-(bicyclo[2.2.1]- .

Signed and Sealed this

Twenty-sixth Day of September, 2006

JON W. DUDAS
*Director of the United States Patent and Trademark Office*